United States Patent [19]

Vann et al.

[11] Patent Number: 5,181,903
[45] Date of Patent: Jan. 26, 1993

[54] METHOD FOR IMPROVING A BIOMATERIAL'S RESISTANCE TO THROMBOSIS AND INFECTION AND FOR IMPROVING TISSUE INGROWTH

[75] Inventors: Richard D. Vann; Wayne A. Gerth, both of Durham, N.C.

[73] Assignee: Duke University, Durham, N.C.

[21] Appl. No.: 173,635

[22] Filed: Mar. 25, 1988

[51] Int. Cl.$^5$ .......................... A61F 2/06; A61F 2/54
[52] U.S. Cl. ........................................ 600/36; 623/1; 623/901; 128/DIG. 22
[58] Field of Search ...................... 623/1, 11, 12, 901; 600/36; 128/DIG. 22

[56] References Cited

U.S. PATENT DOCUMENTS

| | | | |
|---|---|---|---|
| 4,164,524 | 8/1979 | Ward et al. | 128/DIG. 22 |
| 4,193,138 | 3/1980 | Okita | 623/1 |
| 4,265,927 | 5/1981 | Ericksson et al. | 623/1 |
| 4,612,337 | 9/1986 | Fox, Jr. et al. | 623/1 |
| 4,902,290 | 2/1990 | Fleckenstein et al. | 623/1 |
| 4,911,713 | 3/1990 | Sauvage et al. | 623/1 |
| 4,941,871 | 7/1990 | Ward | 600/36 |

OTHER PUBLICATIONS

Osada et al, Am. J. Physiol.: Heart Circ. Physiol. 234:H646-652 (1978).
Trudell et al, Trans. Am. Soc. Artif. Intern Organs 24A:320 (1978).
Madras et al, Trans. Am. Soc. Artif. Intern Organs, 26:153-157 (1980).
Ward et al (Trans. Am. Soc. Art. Int. Org. 20:77-84 (1974)).
Ward and Forest (Ann. Biomed. Eng. 4:184-207 (1976)).
Nichols et al, Circulation 70:843-850 (1984).
Bennegard et al, Act Anaesth. Scand. 26:112-120 (1982).
Lin et al, Trans. Am. Soc. Artif. Intern. Organs 31:468-473 (1985).
McRea et al, Trans. Am. Soc. Artif. Intern. Organs 27:511-516 (1981).
Noishiki et al, Trans. Am. Soc. Artif. Intern. Organs 27:213-218 (1981).
Hoffman et al, Trans. Am. Soc. Artif. Intern. Organs 18:10-17 (1972).
Mori et al., Trans. Am. Soc. Artif. Intern. Organs 24:736-745 (1978).
Greco and Harvey, J. Surg. Res. 36:237-243 (1984).
Trooskin et al, Surgery 97:547-551 (1985).
Eddy et al, Plas. Reconstr. Surg. 78:504-512 (1986).
McRea and Kim, Trans. Am. Soc. Artif. Intern. Organs 24:746-752 (1978).
Ritter et al, "Hydrostatic Pressure Reduces Thrombogenicity of Polytetrafluoroethylene Vascular Grafts", 1989 the American Physiological Society, pp. H1076-1081.
Bensen et al, "Quantification of Gas Denucleation and Thrombogenicity of Vascular Grafts" Journal of Biomedical Materials Research, vol. 25, 373-386 (1991).

*Primary Examiner*—Paul Prebilic
*Attorney, Agent, or Firm*—Cushman, Darby & Cushman

[57] ABSTRACT

This invention relates to a method for improving the resistance of biomaterial to thrombosis and infection and for improving tissue ingrowth, by eliminating undissolved gasses therefrom and by incorporation of therapeutic agents therein via the application of hydrostatic pressure.

28 Claims, 4 Drawing Sheets

METHOD FOR IMPROVING A BIOMATERIAL'S RESISTANCE TO THROMBOSIS AND INFECTION AND FOR IMPROVING TISSUE INGROWTH

FIELD OF THE INVENTION

This invention relates to a method for improving the resistance of biomaterial to thrombosis and infection and for improving tissue ingrowth, by eliminating undissolved gasses therefrom and by incorporation of therapeutic agents therein via the application of hydrostatic pressure.

BACKGROUND OF THE INVENTION

Synthetic vascular prostheses have been widely utilized in clinical medicine as conduit replacements and bypasses for large and small vessels in patients with inadequate autogenous replacement vein due to prior chemotherapy, previous harvest, phlebitis or other vascular pathologies. The use of synthetic vascular prostheses, particularly for microvascular reconstruction, coronary and below knee bypass grafting, has not been entirely satisfactory, however, due to the high rate of short-term thrombosis and long-term intimal hyperplasia associated with their use. Therefore, the need exists for synthetic vascular prostheses whose biocompatibility and performance approaches that of autogenous vein.

While a number of techniques have been employed to improve the patency of synthetic vascular prostheses, including the topical and systemic application of antiplatelet agents and the use of arteriovenous fistulas, satisfactory results have yet to be achieved. The failure of these techniques to attain prolonged patency in synthetic grafts is due no doubt to their inability to remedy or even alleviate one of the primary causes of prosthesis associated thrombogenicity, the presence of trapped gas on the synthetic surface and the resulting formation upon implant of a significant area of blood-gas interface.

Although the mechanism of prosthesis associated thrombosis is not completely understood, one major factor implicated in triggering thrombogenesis on biomaterials, and one overlooked by most researchers in the field, is the presence of small pockets of undissolved gas trapped in or on surfaces, crevices, fissures, and other asperities and within the structural matrices of synthetic materials. These gas pockets, which may be macroscopic or microscopic in size, have been termed gas nuclei. Scanning electron micrography of vascular prostheses has demonstrated that disproportionate platelet adhesion generally occurs at the site of nuclei entrapment.

Early studies with bubble and rotating disc oxygenators have shown that direct contact with gaseous oxygen is damaging to various blood components. For instance, the formation of blood-gas interfaces cause plasma protein denaturation, which in turn leads to sludging, clotting factor activation, alteration of immune system functions, activation of the complement system and the production of lipid emboli. From these and related observations it became clear that the formation of blood-gas interfaces on implanted biomaterials, due to the direct contact of blood with undissolved gas nuclei, could lead to thrombosis, and result in a significant decrease in the patency of the biomaterial.

Gas nuclei, which contribute to the formation of a blood-gas interface, have since been shown to cause thrombus formation on many synthetic biomaterials. Thrombi resulting from trapped gas nuclei are especially prevalent and problematic in biomaterials such as expanded polytetrafluoroethylene (PTFE), which are commonly used in small caliber prostheses. PTFE is, in fact, one of the most widely used of the microvascular graft materials. By way of example, the high rate of thrombosis associated with the use of PTFE may be best explained by its hydrophobicity and its microporous or fibril structure in which a large gas volume is trapped. These are both factors which have been found to contribute significantly to the presence and stability of gas nuclei.

The ability of a surface, particularly a porous surface, to trap gas once it is immersed in a liquid is directly related to the material's hydrophobicity and to the nature of the surrounding liquid. For instance, a non-polar liquid can enter a pore or crevice in a hydrophobic material more easily than an aqueous liquid can and thereby displace any gas which may be trapped within. Hydrophobic, microporous PTFE contains about 70% gas by volume and has an 80% internal gaseous surface area. Immersion of PTFE in water for one month displaces only 10% of the undissolved gas trapped on the material's surface and within its structural matrix. PTFE immersion in a non-polar compound such as acetone, however, displaces 95–97% of the trapped gas within 24 hours.

Numerous methods have been employed with varying degrees of success to extract trapped gas from biomaterials. These processes are generally known as priming techniques. When these methods are successful in ridding the material of gas nuclei, the term "denucleation" has been coined and may be more appropriate.

The basic objective of denucleation is the replacement of the gas nuclei with a bio- or hemocompatible solution. Denucleation serves to prevent the formation of blood-gas interfaces by largely or totally displacing the undissolved gas from the material. This prevents contact between the blood and the gas and thereby reduces or eliminates the blood-gas interface. Some priming techniques which have been previously employed to exclude air from a material prior to use include vacuum and carbon dioxide exposure, as well as saline, degassed saline, ethanol and acetone soaking. See generally, Osada et al., Am. J. Physiol.: Heart Circ Physiol. 234:H646–652 (1978); Kolobow and Tomlinson, J. Biomed. Mater. Res. Vol. 11, pp. 471–481(1977); Trudell et al., Trans. Am. Soc. Artif. Intern Organs 24A:320 (1978); and Madras et al., Trans. Am. Soc. Artif. Intern. Organs, 26: 153–157 (1980)).

Due to the porosity and hydrophobicity of many of the synthetic prostheses currently in use (e.g., PTFE), it was not surprising to find that the standard priming techniques, namely saline and degassed saline priming, were for all practical purposes completely ineffective at removing the gas nuclei from these biomaterials (Madras et al.). Vacuum, ethanol and acetone priming were shown to be more effective than saline or degassed saline priming, but these techniques and solutions were generally cumbersome, time consuming and/or resulted in only partial denucleation. For example, Ward et al. (Trans. Am. Soc. Art. Int. Org. 20:77–84 (1974)) and Ward and Forest (Ann. Biomed. Eng. 4:184–207 (1976)) demonstrated that vacuum priming of a silicone tube in a buffer solution at an absolute pressure of 1 torr for 20 hours was sufficient to remove enough gas nuclei to reduce platelet adhesion by 90%. This technique was ineffective, however, at removing gas nuclei which were trapped in crevices smaller than 2 microns.

Unlike vacuum priming, acetone priming has been shown to be quite efficient at removing even small gas nuclei from hydrophobic materials, but a subsequent soaking and flushing period is required during which time the acetone itself must be displaced from the denucleated material and replaced with saline, water, or other biocompatible liquids.

Priming of biomaterial, in this case PTFE, with ethanol has been shown to be significantly less effective at eliminating trapped gas than priming with acetone. Denucleation of PTFE with ethanol was incomplete even after 7 days of immersion. A 20 minute low pressure ethanol soak, while only partially effective in denucleating PTFE, was nonetheless found to improve the "effective porosity" of the material and to permit better tissue ingrowth. See, Trudell et al., and Madras et al.

In addition to increasing patency by employing denucleation techniques to reduce the formation of prosthesis associated-thrombi caused by undissolved gas nuclei, other methods for increasing patency have been attempted as well. For example, some investigators have tried to mimic the natural endothelium anti-thrombogenicity which is achieved at least partially in vivo due to its secretion of prostacyclin, a powerful anti-platelet agent. Processes which have been applied and tested both in vitro and in vivo with some success include the binding of anticlotting factors and antithrombogenics such as heparin, prostaglandins, serum albumin, and streptokinase in layers to the surface of prostheses. See e.g., Nichols et al., Circulation 70:843-850 (1984); Bennegard et al., Acta Anaesth. Scand. 26:112-120 (1982); Lin et al., Trans. Am. Soc. Artif. Intern. Organs 31:468-473 (1985); McRea et al., Trans. Am. Soc. Artif. Intern. Organs 27:511-516 (1981); Noishiki et al., Trans. Am. Soc. Artif. Intern. Organs 27:213-218 (1981); McRea and Kim, Trans. Am. Soc. Artif. Intern. Organs 24:746-752 (1978); Hoffman et al., Trans. Am. Soc. Artif. Intern. Organs 18:10-17 (1972); and Mori et al., Trans. Am. Soc. Artif. Intern. Organs 24:736-745 (1978).

In addition to antithrombotic therapeutics, agents bearing other therapeutic qualities have also been used in conjunction with synthetic biomaterials in order to reduce or alleviate disorders causally related to thrombi formation, as well as those generally associated with the use of synthetic prostheses. For instance, the risk of infection always exists when artificial substances are introduced into the body, and occurs preferentially at thrombotic sites. The likelihood of infection has been significantly reduced, however, when anti-viral and/or anti-bacterial therapeutics (collectively known as antibiotics) have been incorporated onto the surface or into the matrices of biomaterials used as sutures, catheters, and vascular prostheses. Greco and Harvey, J. Surg. Res. 36:237-243 (1984); Trooskin et al., Surgery 97:547-551 (1985); and Eddy et al., Plas. Reconstr. Surg. 78:504-512 (1986). Previous techniques stored such therapeutics in a layer bound to the surface of the biomaterial. These agents then diffused or were released from the bonding media over a period of hours or days.

SUMMARY OF THE INVENTION

The present invention overcomes the problems and disadvantages of the prior art by providing an effective means for improving a biomaterial's resistance to thrombosis and infection and for improving tissue ingrowth, by eliminating undissolved gas from the surface and matrices of biomaterials by the application of hydrostatic pressure, thereby improving tissue ingrowth and preventing the formation of a blood-gas interface which triggers and/or promotes thrombosis and infection, and further by incorporating therapeutic agents into and on the matrix and surface of a biomaterial in order to actively combat thrombogenesis and infection.

The objects of the present invention are as follows: (1) to improve a biomaterial's resistance to thrombosis and infection; (2) to improve tissue ingrowth; (3) to increase the patency rate and hemocompatibility of biomaterial, particularly biomaterial used in vascular prostheses; (4) to provide an effective means for eliminating all or substantially all undissolved gas from a biomaterial; and (5) to provide a means for supplying therapeutic agents to a biomaterial.

Additional objects and advantages of the invention will be set forth in the description which follows. They may be obvious from the description itself, or may be learned by practice of the invention. The objects and advantages of the invention can be realized and attained by means of the instrumentalities and combinations particularly pointed out in the appended claims.

To achieve the objects and in accordance with the purposes of the present invention, as embodied and broadly described herein, a method for improving a biomaterial's resistance to thrombosis and infection and for improving tissue ingrowth is disclosed which comprises the application of hydrostatic pressure to a biomaterial while it is submerged in a liquid, at a pressure and for a time sufficient to denucleate the biomaterial by displacing and/or dissolving all, or substantially all, gas from the biomaterial with the liquid.

To further achieve the objects and in accordance with the purposes of the present invention, as embodied and broadly described herein, a method for improving a biomaterial's resistance to thrombosis and infection and for improving tissue ingrowth is disclosed which comprises the application of hydrostatic pressure to a biomaterial while it is submerged in a liquid including gels or gel-forming sols, at a pressure and for a time sufficient to denucleate the biomaterial by displacing and/or dissolving all, or substantially all, gas from the biomaterial with the liquid containing one or more therapeutic agents. If the liquid is a gel-forming sol, the sol is then polymerized on the surface and within the structural matrix of the denucleated biomaterial.

An additional aspect of the present invention is the product of the disclosed process.

The method of the present invention involves placing a biomaterial in a liquid to which absolute pressure is applied hydrostatically, i.e., by compression of the biomaterial with a liquid rather than with a gas, so as to prevent an increase in the dissolved gas tension. By increasing the hydrostatic pressure around the biomaterial, the undissolved gas present on the surface or within the structural matrix of the biomaterial is compressed and reduced in volume. Since the pressure in the gas phase is much higher than the dissolved gas tension, the undissolved gas molecules making up the gas nuclei diffuse from the gas phase into the liquid phase, and the gas phase is gradually eliminated by dissolution into the liquid phase. Then the space formerly filled by the gas nuclei is occupied by the submersion liquid. For purposes of the present invention we term this event displacement and/or dissolution.

Once gas nuclei have been displaced and/or dissolved from a material according to the disclosed process, they will not reform as long as the material is stored in a liquid which is not supersaturated with gas. Brief exposure periods in air are possible without reintroducing gas into the denucleated material, if the material is well irrigated. While in air, care should be exercised to avoid bending or stretching the denucleated material as this could draw fresh gas into the material.

Heating the submersion liquid, or boiling it under vacuum reduces the initial dissolved gas tension and thereby accelerates the dissolution of gas nuclei when the hydrostatic pressure is raised. As gas also dissolves in some biomaterials, it is helpful to expose the materials to vacuum to eliminate the dissolved gas. A material so treated may then be placed in degassed liquid while under vacuum to prevent additional gas from entering the pores and matrix of the material by compression to sea level pressure with gas. This method provides the greatest possible decrease in gas volume upon application of hydrostatic pressure above sea level pressure.

In addition, the use of surfactants or other liquids such as ethanol or acetone can further accelerate the penetration of liquid into gas containing pores and thereby promote the elimination of gas nuclei from biomaterials. The use of surfactants to allow the liquid to better wet the biomaterial can assist liquid penetration and elimination of undissolved gas.

DESCRIPTION OF THE DRAWINGS

Table 1 depicts the patency rate of 13 P and 4 NP expanded PTFE grafts (1 mm×28 cm) which were inserted into rats with the right proximal carotid serving as the inflow to the graft, and the distal left carotid serving as the outflow from the graft.

DESCRIPTION OF THE PREFERRED EMBODIMENTS

Reference will now be made in detail to the preferred embodiments of the present invention.

The invention comprises a method for improving a biomaterial's resistance to thrombosis and infection and for improving tissue ingrowth. Many biomaterials are contemplated for treatment by the present invention, including those used as catheters, vascular prostheses, sutures, auxiliary circulation plumbing devices, artificial organs, porous implant materials, artificial heart valves, total artificial hearts, and mammary implants to name but a few. Those skilled in the art are familiar with the considerations which may be involved in the selection of a biomaterial suitable for use in a specific application. For purposes of the present invention, any biomaterial suitable for the uses described above may be employed in the invention.

While the fundamental nature of biocompatibility is not fully understood, hydrophobicity and chemical inertness are characteristics frequently believed to increase a material's bio- and hemocompatibility. Structural considerations such as porosity also are determinative of a biomaterial's suitability for use in a particular bioapplication, due to the fact that porous materials generally achieve improved tissue ingrowth and reduced encapsulation over nonporous materials.

Therefore, and in accordance with the present invention, the biomaterial may be selected from polytetrafluoroethylene (PTFE, both expanded and monolithic), silicone rubber, polyurethane, DACRON, steel, pyrolytic carbon, porous implant material, and other materials suitable for implant in humans or animals. As embodied herein, the biomaterial is preferably one selected from those suitable for use in macro-and microvascular prostheses. More preferably the biomaterial is expanded PTFE which, due to its structural and chemical characteristics, enjoys widespread use in vascular prostheses where resistance to thrombosis and infection is particularly critical due to the small caliber of the material employed.

To improve the biomaterial's resistance to thrombosis and infection and to improve tissue ingrowth, the method of the present invention contemplates the application of hydrostatic pressure to the biomaterial while it is submerged in a liquid. When hydrostatic or fluid compression pressure is applied to a submerged material, the undissolved gas nuclei on the surface and within the structural matrix of the material are compressed, causing them to diffuse into and to be displaced by the liquid in which the material is submerged. The surface and matrix of the material then act as storage depots for the solution and any compounds dissolved or dispersed therein.

Numerous liquids are contemplated for use in the present invention including crystalloids such as water, saline and lactated Ringer's solution, low surface tension solvents such as ethanol and acetone, and surfactants. In addition, the liquid is also contemplated as comprising a gel or a gel-forming sol which, upon application of hydrostatic pressure, incorporates or binds to the surface and in the matrix of the biomaterial, thereby providing a more permanent storage depot for compounds which are dissolved or dispersed therein. As the internal surface area is also available for binding and storage, an increased quantity of therapeutic agent can be provided thereto.

In accordance with the present invention, therefore, the liquid may be selected from saline, lactated Ringer's solution, ethanol, acetone, sodium alginate, agarose, vinyl acetate, polyacrylamide, surfactants, aqueous and non-aqueous solutions, emulsions, polymers, and suspensions. As embodied herein, the liquid comprises saline or sodium alginate, a gel-forming sol. As employed in a present embodiment, the biomaterial is submerged in a sodium alginate sol which, after completion of the denucleation process, is then polymerized in and on the denucleated biomaterial.

When sodium alginate or other gel-forming sols are employed as submersion liquids, it is contemplated that the sol incorporated on and in the pressurized biomaterial will be polymerized immediately upon removal of the biomaterial from the pressurization apparatus, or sometime thereafter, in order to prevent renucleation as well as to retain an optimal amount of the sol (and any compounds dispersed or dissolved therein) on the surface and in the matrix of the pressurized biomaterial. As an example, when a biomaterial is hydrostatically pressurized in a sodium alginate sol, removing the pressure-treated material from the sol and subsequently submersing it in a liquid containing calcium ions will polymerize the sol, and thereby incorporate the sodium alginate/calcium complex (gel) on and in the denucleated biomaterial.

While the elimination of undissolved gas from a biomaterial by the application of hydrostatic pressure thereto results in a passive reduction of thrombogenicity and an increase in tissue ingrowth potential, biomaterials may also be made to exhibit active thromboresistance by the incorporation of therapeutic agents thereon and therein.

Therapeutic agents used in the invention may consist of antithrombogenics such as heparin which limits fibrin deposition, and prostacyclin which blocks platelet activation, anti-viral and anti-bacterial agents (antibiotics) which eliminate, alleviate, or increase resistance to infection, as well as other modalities. Incorporation of therapeutics in and on biomaterials is beneficial, for they can lessen many problems and risks associated with the use of biomaterials including thrombogenesis and infection (which occurs preferentially at thrombotic sites).

Numerous agents possessing various therapeutic activity are contemplated for use in the present invention. By way of example, compositions containing prostacyclin, prostacyclin analogs and derivatives thereof are suitable for use when an antithrombogenic therapeutic agent desired. Of these, Iloprost ® TM (Schering AG, Berlin, West Germany), a stable, ethanol and water soluble, synthetic prostacyclin analog is but one example. Heparin is a second example (Sigma, St. Louis, Mo.). In addition, numerous other antithrombogenics or antithrombolytics such as streptokinase, tissue plasminogen activator (TPA), and urokinase which alleviate or limit clotting, fibrin deposition and platelet adhesion are also suitable for use.

In addition, therapeutic agents bearing bacteriostatic or bactericidal characteristics (antiviral characteristics too) may also be employed. These agents may include cephazolins, cephamandol, penicillins, penicillin derivatives, aminoglycosides, as well as other compounds functionally related to those previously listed. It is also feasible to incorporate biological therapeutics such as living endothelial cells into biomaterials according to the process disclosed herein.

Upon incorporation or polymerization in and on the biomaterial, it is contemplated that a therapeutic containing liquid will release the therapeutic agent dissolved or dispersed therein by diffusion or other means of gradual or continuous release. For example, while the polymerized sodium alginate/calcium liquid is relatively stable, under physiological conditions the agents diffuse out of the gel and the gel slowly reconverts to a sol. This results in the gradual release of any dissolved or dispersed therapeutics therein.

In accordance with the present invention it is therefore further contemplated that the liquid may contain one or more therapeutic agents dissolved or dispersed therein. The therapeutic agents may consist of antithrombogenics or antibiotics. These may be selected from heparin, chondroitin sulfate, charonin sulfate, antiplatelet agents, urokinase, prostacyclin, prostacyclin analogs, Iloprost TM, streptokinase, tissue plasminogen activator (TPA), bacteriostatic, bactericidal and antiviralagents, cephazolins, cephamandol, penicillins, penicillin derivatives, aminoglycosides, and functionally related modalities, including endothelial cell suspensions. As embodied herein, one or more therapeutic agents are preferentially dissolved or dispersed within a liquid comprising a gel-forming sol.

To improve the biomaterial's resistance to thrombosis and infection, and to improve its tissue ingrowth potential, the method of the present invention contemplates the application of hydrostatic pressure to a biomaterial while it is submerged in a liquid, at a pressure and for a time sufficient to denucleate the biomaterial by displacing and/or dissolving all, or substantially all, undissolved gas from the biomaterial with the liquid. Prior to denucleation, liquids of choice may preferentially be vacuum degassed. They may then be flushed through the matrix of porous materials.

Hydrostatic pressures of 3000, 6000 and 20,000 psig (pounds per square inch gauge) have been found to be effective in eliminating gas nuclei from biomaterials. The time periods required to eliminate gas nuclei vary, however, and depend on such factors as material size and liquid volume. For example, the ratio of the liquid to material volume should be large in order to minimize the rise in gas tension which occurs as gas dissolves in the submersion liquid. Because of this rise, and because gas at high pressure dissolves in some biomaterials, it is sometimes necessary to conduct multiple compressions with fresh, degassed liquid. Also, since there is no convective mixing near the gas phase as it diffuses into surrounding liquid (particularly in the lumen of a vascular graft), local regions of high gas concentration can develop. Small pieces of material such as 1 mm vascular prostheses can be degassed in an hour at a pressure in the range of about 3000 to about 6000 psig, while larger, thicker grafts can require multiple compressions at 20,000 psig, the total compression period lasting up to several days.

In accordance with the present invention hydrostatic pressure is applied to a biomaterial submerged in a liquid in a range of from about 3000 to about 20,000 psig. The period may range from less than about 1 hour to more than about 72 hours. As embodied herein, hydrostatic pressure is applied to a small caliber prosthesis approximately 1 mm in diameter and about 0.3, 1.5, and 28 cm in length, in a range of from about 3000 to about 6000 psig, for a period ranging from about 1 hour to about 6 hours.

The preferred embodiment of the method of the present invention generally comprises the following steps:

1. Degassing the liquid in a high vacuum.
2. Degassing the biomaterial in a high vacuum.
3. Submerging the degassed biomaterial in the degassed liquid while both are in a high vacuum, in order to remove as much gas as possible and to prevent the reentry of new gas, either dissolved or undissolved.
4. Compression of the submerged biomaterial hydrostatically to a pressure of up to about 20,000 psig, for up to 72 hours, or as long as is necessary to denucleate the biomaterial by displacing and/or dissolving all, or substantially all, gas therefrom.
5. Use of surfactants or non-aqueous liquids to assist penetration of liquid in the biomaterial and displacement and/or dissolution of the gas is contemplated.
6. Dissolution or dispersion of therapeutic agents in the submersion liquid to combat thrombosis, infection, or other undesirable conditions is also contemplated.

7. Use of a gel or a gel-forming sol as the submersion liquid to seal the matrix of a porous biomaterial and to trap or bind the therapeutic agents on or in the denucleated biomaterial is further contemplated.

The preferred embodiments will be further clarified by the following examples, which are intended to be purely exemplary of the invention.

EXAMPLE 1

Fifteen paired sets of PTFE grafts (Gore-Tex TM, W. L. Gore & Associates, Inc., Flagstaff, Ariz.) 1 mm in diameter and 1.5 cm in length were placed simultaneously in the femoral arteries of rats. One graft sample was denucleated prior to use, while the second was not. To maintain the sterility of the graft sample during pressurization, the sample was placed in a sealed flexible container which permitted the transmission of the hydrostatic pressure to the pressurizing liquid, in this case saline. Hydrostatic pressure of 3000 psig was applied for 1 hour. The liquid to material volume was approximately 200 to 1.

The hydrostatic pressure removed all, or substantially all the undissolved gas from the graft sample, thereby rendering it transparent and pliable. Since significant evaporation is required to reintroduce gas nuclei into a pressure-treated material, the grafts were stored in saline and remained denucleated prior to, and during application and use.

Adult male rats (Charles River, Raleigh, NC) weighing between 350 and 550 g were anesthetized intraperitoneally with sodium pentobarbital (50 mg/kg). 0.2 cc of antibiotic was administered to the rats prophylactically twice daily, 1 day preoperatively and 1 day postoperatively. Both femoral arteries were exposed in each rat, and 1 cm segments of the femoral vessels were removed and replaced with 1 mm×1.5 cm samples of PTFE. Each animal served as its own control having pressurized (P) and non-pressurized grafts (NP) placed on alternate femoral arteries using standard sterile microvascular techniques.

Thrombosis and patency (i.e., the closing off of the vessel due to thrombosis) were assessed for both the P and the NP ("control") grafts using the flicker test, a visual observation of pulsatile flow in graft. The data were statistically analyzed using the Fisher's Exact Test, an accepted method of analysis for binary data.

Fourteen NP grafts thrombosed and lost patency within 10 minutes of implant, while the fifteenth thrombosed within 60 minutes of implant. Fourteen of the fifteen P grafts were patent seven days after implantation. Patency between the two groups was statistically different at $p<0.001$ ($p<0.05$ is generally considered to be the upper limit for statistical significance.) These results are reported in Demas et al., Plastic and Reconstructive Surgery (accepted for publication 1988) which is incorporated herein by reference.

EXAMPLE 2

Seventeen viral-free, male rats (Charles River, Raleigh, NC) ranging in weight from 550 to 650 g were anesthetized intraperitoneally with sodium pentobarbital (50 mg/kg). The neck and left groin areas were prepped, and the rats were placed on warming pads. A midline neck incision was made and a tracheostomy constructed with the insertion of PE-50 polyethylene tubing connected to a ventilator. The femoral vein was then cannulated with a 23 gauge catheter through which 2 ml of saline was infused every hour.

A subcutaneous pocket was formed over the chest wall working through the neck incision with sharp and blunt dissection. Both carotid arteries were mobilized and bathed in 1% lidocaine TM. The right carotid was ligated distally and the left carotid proximally. Microvascular clamps were placed proximally on the right carotid and distally on the left carotid. The arteries were sharply divided 0.5 cm from the ligatures and the lumens were irrigated free of blood with saline.

PTFE grafts 1 mm×28 cm were interposed with interrupted stitches of 10-0 suture material using standard sterile microvascular technique so that the right proximal carotid served as the inflow and the distal left carotid served as the outflow. Thirteen of the rats were implanted with pressurized (P) graft material treated as in Example 1, while 4 rats served as controls and were implanted with non-pressurized (NP) graft material. The anastomoses were performed with saline irrigation covering both the internal and external surfaces of the conduit. Patency was assessed at 1, 5, 30 and 60 minutes, and hourly thereafter, using the flicker test.

The four NP grafts were patent for less than 5 minutes, while the mean time of patency for the 13 P grafts was 5.5 hours (±0.4 hours standard error). These results are depicted in Table 1.

TABLE 1

| Period of Patency (Hours) | Degree of Denucleation |
| --- | --- |
| 8.0 | ++++ |
| 6.5 | ++++ |
| 6.5 | +++ |
| 6.0 | ++++ |
| 6.0 | ++ |
| 5.5 | ++++ |
| 5.5 | ++ |
| 5.0 | ++++ |
| 4.5 | ++++ |
| 4.5 | ++ |
| 4.0 | ++ |
| 4.0 | + |
| 3.0 | ++ |
| <.083 | — |
| <.083 | — |
| <.083 | — |
| <.083 | — |

Degree of denucleation: ++++ = Excellent; +++ = Good; ++ = Fair; + = Poor; — = No denucleation. Determination was made by qualitative visual estimation based upon the degree of transparency of the treated graft.

EXAMPLE 3

Figure 1:
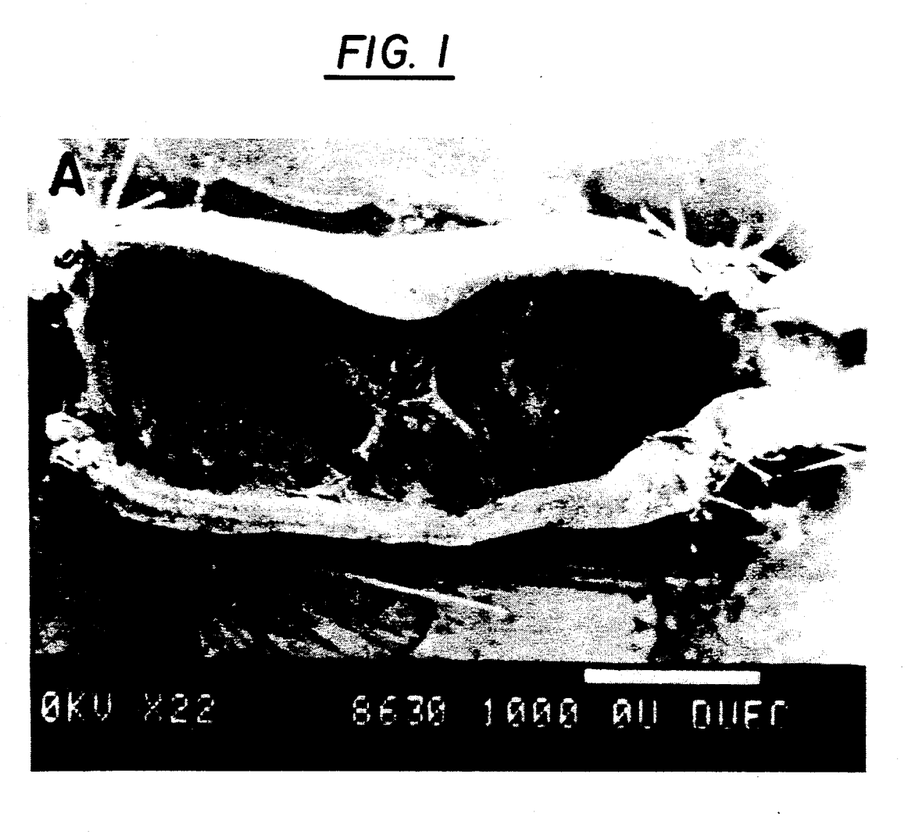
FIG. 1 is a 22× magnification by scanning electron microscopy of non-pressurized (NP) PTFE graft (1 mm×3 mm) shown 48 hours after insertion into the carotid position of the rat.
Figure 2:
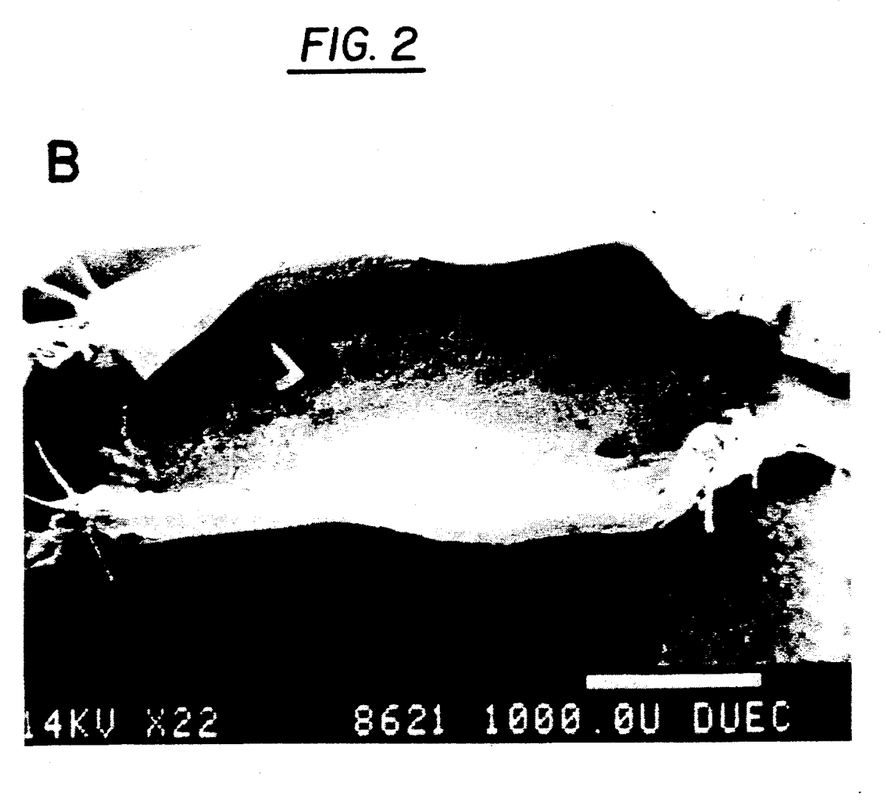
FIG. 2 is a 22× magnification by scanning electron microscopy of pressurized (P) PTFE graft (1 mm×3 mm) shown 48 hours after insertion into the carotid position of the rat.
Figure 3:
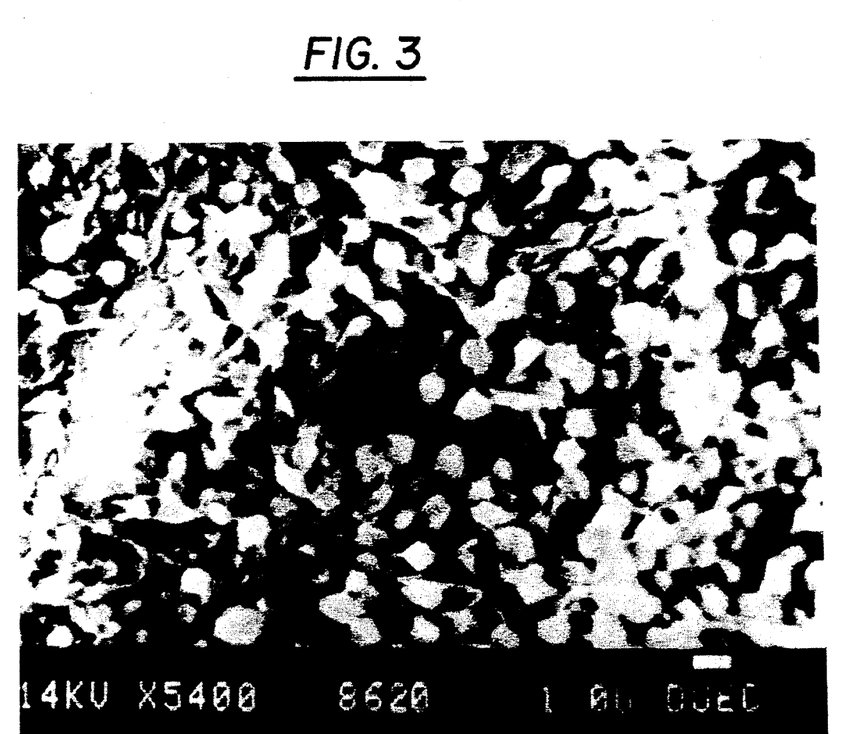
FIG. 3 is a 5400× magnification by scanning electron microscopy of NP PTFE graft (1 mm×3 mm) shown 48 hours after insertion into the carotid position of the rat.
Figure 4:
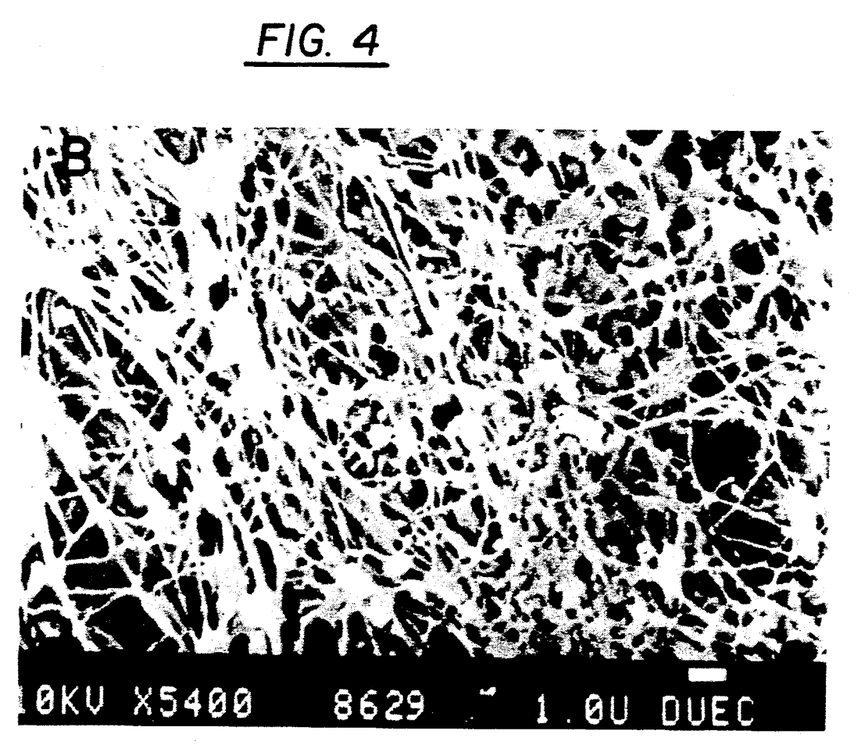
FIG. 4 is a 5400× magnification by scanning electron microscopy of P PTFE graft (1 mm×3 mm) shown 48 hours after insertion into the carotid position of the rat.

A PTFE graft (1 mm×0.3 cm) pressurized according to Example 1, and an unpressurized PTFE graft (1 mm×0.3 cm) were placed in the carotid position of the rat using sterile microvascular technique. Forty-eight hours after implant the grafts were removed and processed for scanning electron microscopy. The results, which are depicted in FIGS. 1-4, are summarized below.

The NP graft (FIG. 1) showed thrombus formation at its center (magnification 22×), while the P graft (FIG. 2) was clot free, the box-like structure is an artifact of the electron microscopy preparation process. Higher magnification of 5400× showed the NP graft to have significant platelet adhesion (FIG. 3), while the P graft (FIG. 4) appeared to be covered by a fibrin mat.

EXAMPLE 4

The right and left carotid arteries of 5 rats were mobilized under sodium pentobarbital anesthesia, and reconstructed by interposing 5 mm lengths of 1 mm diameter expanded PTFE vascular graft therein. In each rat a P and NP graft were introduced. The P graft was treated generally as in Example 1, with the following exception: hydrostatic pressure was applied at 6000 psig for a period of 2 hours.

After completion of the anastomoses using standard sterile microsurgical technique, with interrupted stitches of 10-0 suture material, the microvascular clamps were removed and the grafts perfused with blood for 5 minutes. A 0.1 ml sample of a solution containing 111 Indium labeled human platelets was then injected into the grafts. After perfusion for 1 hour with these platelets, the chest was opened and an 18 gauge needle connected to a chilled bag of lactated Ringer's solution, was inserted into the left ventricle of the rat's heart. The descending aorta was clamped and 50 ml of Ringer's solution was infused into the proximal aorta and its branches, thereby clearing them of blood. The grafts were harvested and placed in a well counter for gamma counting.

The background counts were measured and subtracted from the values measured for each graft. The ratio of counts for the NP versus the P grafts were determined for each rat. The mean ratio for all animals was 3.96 to 1. This represented a 75% (±5% Standard Deviation) lower platelet adhesion in the P over the NP grafts.

EXAMPLE 5

Four PTFE samples 1 mm × 1.5 mm were pressurized according to the general procedure set forth in Example 1 with the following variations. Pressure was applied for 2-8 hours at 6000 psig in a 1% sodium alginate sol (Sigma, St. Louis, Mo.) in which heparin (Sigma, St. Louis, Mo.) and Iloprost TM (Schering AG, Berlin, West Germany) (0.1% in phosphated buffer adjusted to pH 7.4 with NaOH) had been dissolved. After pressurization, the grafts were placed over intravenous catheters and transferred to a 10% solution of calcium chloride for 10 minutes. The calcium ions in this solution converted the sodium alginate sol to a calcium alginate gel. The catheters were removed, and the grafts were allowed to remain in the calcium chloride for an additional 30 minutes. The grafts were then removed and rinsed in lactated Ringer's solution.

Ten control grafts were also prepared which consisted of unpressurized, untreated grafts (NP), grafts pressurized in saline (P), and grafts pressurized in sodium alginate (sol) without heparin or Iloprost TM, and polymerized in calcium chloride (PA).

The pressurized sodium alginate/heparin/Iloprost TM (PAHI) grafts and the control grafts were applied as femoral vein implants which is a severe test of thrombogenicity because low pressure venous blood flow is known to render venous grafts more susceptible to thrombosis and infection than arterial grafts.

Each of the 10 control grafts, regardless of their treatment, thrombosed after 20 minutes of perfusion with blood. The 4 PAHI grafts, however, were each patent at 24 hours. Two remained patent more than 3 days.

It will be apparent to those skilled in the art that various modifications and variations can be made in the process of the present invention without departing from the scope or spirit of the invention. Other embodiments of the invention will be apparent to those skilled in the art from consideration of the specification and practice of the invention disclosed herein.

It is intended that the specification and examples be considered as exemplary only, with the true scope and spirit of the invention indicated by the following claims.

We claim:

1. A method for improving a biomaterial's resistance to thrombosis and infection and for improving tissue ingrowth comprising the application of hydrostatic pressure to all surfaces of a biomaterial while it is submerged in a liquid, at a pressure and for a time sufficient to denucleate said biomaterial by displacing and/or dissolving all, or substantially all, undissolved gas from said biomaterial with said liquid.

2. The method of claim 1 wherein said liquid is selected from at least one member of the group consisting of aqueous and non-aqueous solutions, gels, gel-forming sols, suspensions, surfactants, and emulsions.

3. The method of claim 2 wherein said liquid is subjected to vacuum pressure to reduce dissolved gas tension prior to application of hydrostatic pressure.

4. The method of claim 1 wherein said hydrostatic pressure is applied in a range of from about 3000 to about 20,000 psig.

5. The method of claim 1 wherein said hydrostatic pressure is applied in a range of from about 3000 psig to about 6000 psig.

6. The method of claim 1 wherein said biomaterial is selected from at least one member of the group consisting of polytetrafluoroethylene, silicone rubber, polyurethane, steel, and pyrolytic carbon.

7. The method of claim 6 wherein said biomaterial is subjected to vacuum pressure to eliminate dissolved gas prior to application of hydrostatic pressure.

8. The method of claim 1 wherein said biomaterial is polytetrafluoroethylene.

9. The method of claim 1 wherein said liquid contains one or more therapeutic agents.

10. The method of claim 9 wherein said therapeutic agents are selected from at least one member of the group consisting of antithrombogenics and antibiotics.

11. The method of claim 9 wherein said therapeutic agents are selected from at least one member of the group consisting of heparin, chondroitin sulfate, charonin sulfate, antiplatelet agents, urokinase, prostacyclin, prostacyclin analogs, streptokinase, tissue plasminogen activator (TPA), bacteriostatic, bactericidal and antiviral agents, cephazolis, cephamandol, penicillins, penicillin derivatives, and aminoglycosides.

12. A method for improving a biomaterial's resistance to thrombosis and infection and for improving tissue ingrowth comprising the application of hydrostatic pressure to all surfaces of a biomaterial while it is submerged in a gel or a gel-forming sol, at a pressure and for a time sufficient to denucleate said biomaterial by displacing and/or dissolving all, or substantially all, undissolved gas from said biomaterial with said gel or said gel-forming sol;

said gel or said gel-forming sol containing one or more therapeutic agents.

13. The method of claim 12 wherein said gel or said gel-forming sol is selected from at least one member of the group consisting of sodium alginate, agarose, vinyl acetate and polyacrylamide.

14. The method of claim 12 wherein said therapeutic agents are selected from at least one member of the group consisting of heparin, chondroitin sulfate, charonin sulfate, antiplatelet agents, urokinase, prostacyclin, prostacyclin analogs, streptokinase, tissue plasminogen activator (TPA), bacteriostatic, bactericidal and antiviral agents, cephazolins, cephamandol, penicillins, penicillin derivatives, and aminoglycosides.

15. The method of claim 12 wherein said hydrostatic pressure is applied in a range of from about 3000 to about 20,000 psig.

16. The method of claim 15 wherein said hydrostatic pressure is applied in a range of from about 3000 to about 6000 psig.

17. The method of claim 12 wherein said biomaterial is selected from the group consisting of polytetrafluoroethylene, silicone rubber, polyurethane, steel and pyrolytic carbon.

18. The method of claim 12 wherein said biomaterial is polytetrafluoroethylene.

19. The method of claim 1 wherein sid liquid is one or more polymer.

20. The method of claim 2 wherein said liquid is combined with one or more polymer.

21. The method of claim 1 wherein said biomaterial is one or more porous tissue implant.

22. The method of claim 6 wherein said biomaterial is one or more porous tissue implant.

23. The method of claim 12 wherein said biomaterial is one or more porous tissue implant.

24. The method of claim 17 wherein said biomaterial is one or more porous tissue implant.

25. The method of claim 9 wherein said therapeutic agents are endothelial cell suspensions.

26. The method of claim 11 wherein said therapeutic agents are combined with endothelial cell suspensions.

27. The method of claim 12 wherein said therapeutic agents are endothelial cell suspensions.

28. The method of claim 14 wherein said therapeutic agents are combined with endothelial cell suspensions.

* * * * *